SUBSTITUTED 2,3-DIHYDRO IMIDAZO[1,2-c]PYRIMIDINES

BACKGROUND OF THE INVENTION

The Ring Index, page 155 (second edition, American Chemical Society, 1960) gives the basic imidazo[1,2-c]pyrimidine structure with a reference to *Ann.,* 432, 120 (1923). Substituted imidazo[1,2-c]pyrimidines are also referred to in the more recent literature; for example, Bartholomew, et al. *J. Med. Chem.,* 19, 814 (1976) gives the preparation of the arabinosyl hypoxanthine and arabinosyl guanine analogs of the imidazo[1,2-c]pyrimidine series. The intermediate compound 7-chloroimidazo[1,2-c]pyrimidine-5(6H)-one is also referred to. None of the compounds disclosed in this publication exhibited significant anti-viral or anti-microbial activity in vitro. West German Pat. No. 2511316 issued Sept. 18, 1975, (Derwent Abstract 64314W/39, 1975) to Eisai KK discloses a group of 2-alkyl-5-alkylmercapto-7-hydroxyimidazo[1,2-c]pyrimidines. They are alleged to be useful as anti-inflammatory or analgesic agents.

A single reference to chloro substituted 2,3-dihydro-imidazo[1,2-c]pyrimidines is available;—see Yanai et al. *Yakugaku Zasshi,* 94, 1503, (1974). Compound XVII on page 1506 is 7-chloro-2,3-dihydroimidazo[1,2-c]pyrimidine hydrochloride. Both the hydrochloride salt and the free base are characterized in Tables I and Table V and analytical data are provided in Table VIII. The corresponding unhydrogenated compound, XXXII, is also disclosed. No utility is set forth therein for these compounds.

SUMMARY OF THE INVENTION

This invention provides substituted 2,3-dihydroimidazo[1,2-c]pyrimidines of the structure

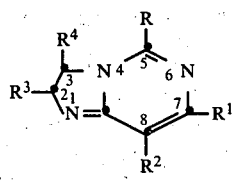

wherein R is $C_1$–$C_5$ alkyl, phenylamino or methylmercapto, $R^1$ is Cl, pyrrolidino, methylamino or N-methylbenzylamino and $R^2$, $R^3$ and $R^4$ individually are H, methyl or phenyl, and pharmaceutically-acceptable acid addition salts thereof formed with strong inorganic acids or strong organic acids such as the organic sulfonic acids.

The illustrative $C_1$–$C_5$ alkyl groups which R can represent include methyl, ethyl, n-propyl, isopropyl, n-butyl, isobutyl, sec-butyl, n-amyl, isoamyl, 1,2-dimethylpropyl, sec-amyl, t-amyl, and the like.

Compounds according to formula I in which $R^1$ is chlorine are weakly basic and form acid addition salts only with strong acids. Pharmaceutically-acceptable acid addition salts of the bases of formula I are thus derived from strong inorganic acids such as: hydrochloric acid, nitric acid, phosphoric acid, sulfuric acid, hydrobromic acid, hydriodic acid, nitrous acid, phosphorous acid and the like. Strong organic acids useful for forming pharmaceutically-acceptable acid addition salts with bases according to formula I when $R^1$ is Cl including particularly the organic sulfonic acids. Pharmaceutically-acceptable salts of this invention thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, benzenesulfonate, toluenesulfonate, chlorobenzenesulfonate, xylenesulfonate, methanesulfonate, trifluoromethyl sulfonate, propanesulfonate, naphthalene-1-sulfonate, naphthalene-2-sulfonate and the like salts.

When $R^1$ in formula I is other than Cl, i.e., is methylamino, pyrrolidino or N-methylbenzylamino, this amine group is quite basic and readily forms acid addition salts with all types of acids, not just strong acids.

Illustrative compounds coming within the scope of this invention include:

5,8-Dimethyl-7-chloro-2,3-dihydroimidazo[1,2-c]pyrimidine sulfate,
2,5-Dimethyl-7-chloro-2,3-dihydroimidazo[1,2-c]pyrimidine hydrobromide,
3,5-Dimethyl-7-pyrrolidino-2,3-dihydroimidazo[1,2-c]pyrimidine nitrate,
3-Methyl-5-methylmercapto-2,3-dihydroimidazo[1,2-c]pyrimidine hydrochloride,
2-Phenyl-5-amino-7-chloro-2,3-dihydroimidazo[1,2-c]pyrimidine dihydrogenphosphate,
2,3,5-Trimethyl-7-chloro-2,3-dihydroimidazo[1,2-c]pyrimidine metaphosphate,
3-Phenyl-7-methylamino-2,3-dihydroimidazo[1,2-c]pyrimidine hydrochloride,
N-methyl-N-benzyl-2-isopropyl-7-amino-2,3-dihydroimidazo[1,2-c]pyrimidine hydrochloride,
N,5-dimethyl-8-phenyl-2,3-dihydroimidazo[1,2-c]pyrimidine-7-amine sulfate,
5-Isoamyl-7-methylamino-2,3-dihydroimidazo[1,2-c]pyrimidine hydrochloride.
5-Phenyl-7-pyrrolidino-2,3-dihydroimidazo[1,2-c]pyrimidine hydrochloride.

The above compounds as well as other compounds coming within the scope of formula I above wherein $R^1$ is chlorine are prepared by the following reaction scheme:

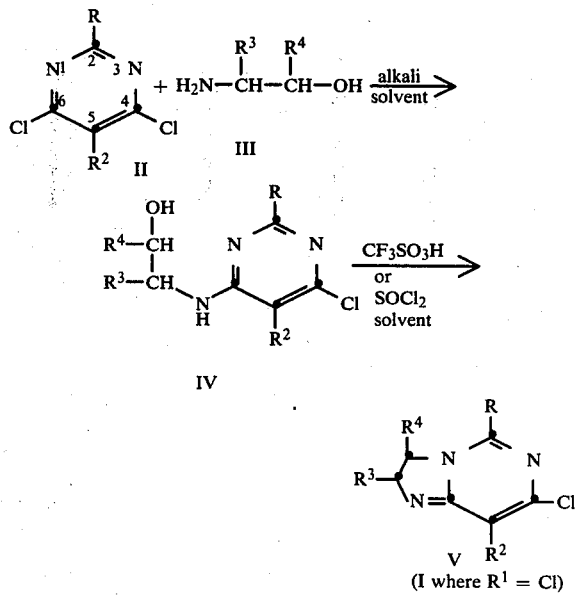

wherein R, $R^2$, $R^3$ and $R^4$ have the same meaning as hereinabove.

United States Patent [19]

Turner

[11] 4,153,695

[45] May 8, 1979

[54] SUBSTITUTED 2,3-DIHYDRO IMIDAZO[1,2-c]PYRIMIDINES

[75] Inventor: William W. Turner, Indianapolis, Ind.

[73] Assignee: Eli Lilly and Company, Indianapolis, Ind.

[21] Appl. No.: 884,884

[22] Filed: Mar. 9, 1978

[51] Int. Cl.² .............. C07D 487/04; A61K 31/505
[52] U.S. Cl. ................................. 424/251; 544/281
[58] Field of Search ......................... 544/281; 424/251

[56] References Cited

U.S. PATENT DOCUMENTS 3,769,288  10/1973  Stähle et al. .............. 260/256.4 F

FOREIGN PATENT DOCUMENTS 2511316  9/1975  Fed. Rep. of Germany ............ 544/281

OTHER PUBLICATIONS

Clark, J. et al., "Heterocyclic Studies", J. Chem. Soc., 1971, (4) pp. 679–683.

Primary Examiner—Donald G. Daus
Assistant Examiner—Lisa Jones
Attorney, Agent, or Firm—James L. Rowe; Arthur R. Whale

[57] ABSTRACT

Di-substituted 2,3-dihydroimidazo[1,2-c]pyrimidines, useful as anti-viral agents.

14 Claims, No Drawings

Analysis Calc.: C, 35.31; H, 3.81; N, 17.65; Cl, 29.77. Found: C, 35.56; H, 3.85; N, 17.64; Cl, 29.98.

By substituting β-hydroxypropylamine for β-hydroxyethylamine in the above example, dl-3,5-dimethyl-7-chloro-2,3-dihydroimidazo[1,2-c]pyrimidine hydrochloride was prepared melting above 150° C. after recrystallization from an ethanol-ethyl acetate solvent mixture.

Analysis Calc.: C, 43.66; H, 5.04; N, 19.09; Cl, 32.21. Found: C, 43.44; H, 4.90; N, 18.22; Cl, 31.93.

By substituting β-phenyl-β-hydroxyethylamine for β-hydroxyethylamine in the above procedure, dl-3-phenyl-5-methyl-7-chloro-2,3-dihydroimidazo[1,2-c]pyrimidine hydrochloride was prepared decomposing above 180° C. after recrystallization from an ethyl acetate ether solvent mixture.

Analysis Calc.: C, 55.34; H, 4.64; N, 14.89; Cl, 25.13. Found: C, 54.96; H, 4.34; N, 14.80; Cl, 25.37.

Also dl-3-phenyl-5-methylthio-7-chloro-2,3-dihydroimidazo[1,2-c]pyrimidine hydrochloride decomposing above 200° C. after recrystallization from an ethanol ethyl acetate solvent mixture.

Analysis Calc.: C, 49.69; H, 4.17; N, 13.37; L Cl, 22.56. Found: C, 49.78; H, 4.11; N, 13.08; Cl, 22.76.

By substituting α-phenyl-β-hydroxyethylamine for β-hydroxyethylamine in the above procedure, 2-phenyl-5-methyl-7-chloro-2,3-dihydroimidazo[1,2-c]pyrimidine hydrochloride was prepared decomposing about 150° C. after recrystallization from an ethanol-ethyl acetate ether solvent mixture.

Analysis Calc.: C, 55.35; H, 4.64; N, 14.89; Cl, 25.13. Found: C, 55.16; H, 4.60; N, 14.68; Cl, 25.12.

EXAMPLE 2

Preparation of 5-Methyl-7-pyrrolidino-2,3-dihydroimidazo[1,2-c]pyrimidine

A reaction mixture was prepared from 2.0 g. of 5-methyl-7-chloro-2,3-dihydroimidazo[1,2-c]pyrimidine hydrochloride and 0.7 g. of pyrrolidine in a saturated aqueous sodium bicarbonate solution. The reaction mixture was allowed to remain at ambient temperature for about three hours, after which time the solvent was removed in vacuo. The resulting residue was heated in ethanol. Solids were separated by filtration and dilute aqueous hydrochloric acid was added to the ethanolic filtrate. The solvent was removed from the filtrate in vacuo to yield 5-methyl-7-pyrrolidino-2,3-dihydroimidazo[1,2-c]pyrimidine hydrochloride formed in the above reaction which decomposed above 245° C. after recrystallization from an ethanol-ethyl acetate solvent mixture.

Analysis Calc.: C, 54.88; H, 7.12; N, 23.27; Cl, 14.73. Found: C, 54.73; H, 7.07; N, 23.03; Cl, 14.97.

By substituting methylamine for pyrrolidine in the above procedure, there was prepared 5-methyl-7-methylamino-2,3-dihydroimidazo[1,2-c]pyrimidine dihydrochloride melting at 250°-253° C. after recrystallization from an ethanol-ethyl acetate solvent mixture.

Analysis Calc.: C, 40.05; H, 5.09; N, 23.06; Cl, 29.09. Found: C, 40.42; H, 5.68; N, 23.70; Cl, 29.50.

Following the above procedure, but substituting N-methyl benzylamine for pyrrolidine, there was prepared N,5-dimethyl-7-benzylamino-2,3-dihydroimidazo[1,2-c]pyrimidine hydrochloride decomposing at 213° C. after recrystallization from ether.

EXAMPLE 3

Preparation of 7-(β-Chloroethylamino)-8-nitro-2,3-dihydroimidazo[1,2-c]pyrimidine A solution of 20 g. of 4,6-dichloro-5-nitropyrimidine was prepared in ether. An aqueous solution containing 14 g. of β-chloroethylamine hydrochloride and 24 g. of sodium bicarbonate were added thereto and the subsequent mixture agitated for about 30 minutes. The ether layer was separated, and the separated layer washed with water and dried. Removal of the ether in vacuo yielded an oil containing chiefly 4-(β-chloroethylamino)-5-nitro-6-chloropyrimidine plus a small quantity of 5-nitro-4,6-bis(β-chloroethyl)pyrimidine (the disubstituted product) and a very small quantity of starting material. The oily residue was allowed to stand in chloroform for about one day. A solid comprising 7-(β-chloroethylamino)-8-nitro-2,3-dihydroimidazo[1,2-c]pyrimidine hydrochloride precipitated and the precipitate was separated by filtration, 7-(β-chloroethyl)amino-8-nitro-2,3-dihydroimidazo[1,2-c]pyrimidine hydrochloride thus prepared decomposed at 135° C. after recrystallization from chloroform; yield=5.378 g.

Analysis Calc.: C, 34.30; H, 3.96; N, 25.00; Cl, 25.31. Found: C, 34.42; H, 3.82; N, 25.08; Cl, 25.59.

The compounds of this invention prepared according to the above procedures were isolated and characterized in the form of the hydrochloride salts. Other salts are prepared by substituting the desired anion for the chloride anion in the particular ion exchange resin employed during the metathetic reaction to replace the trifluoromethylsulfonic acid group.

The compounds of this invention are anti-viral agents and have demonstrated their activity against cutaneous Herpes simplex virus type 1 (HSU-1) in guinea pigs according to the following tests. Three epilated areas on each guinea pig back were inoculated with approximately $1 \times 10^5$ plaque forming units of virus using a Sterneedle triggered 10 times for each area. Untreated guinea pigs so inoculated developed consistent rosette lesions in about 96 hours. All three areas on the back of each guinea pig were drug-treated and these compared with separate control animals which were treated with the particular vehicle employed for administering the drug. The positive control animals were treated with 0.5–1.0 percent phosphonoacetic acid (PAA) suspended in the same vehicle as the drug. Animals were inoculated on the morning of day 1 and treated on the afternoon of day 1. Two treatments per day were administered through day 5 for a total of 10 treatments. Hair was again epilated on day 5 and readings were begun then and taken daily through day 10. Lesions for each area were scored from 0 to 4+, which was a fully developed herpetic lesion with inflammation vesicles and pustules. An average score was then calculated for each drug for each day for the number of treated areas and control areas. Usually 3–6 guinea pigs were used per drug. After scoring, a final score or mean of means was calculated for drug-treated and for control areas. Table I which follows gives the results of determinations carried out as outlined above on compounds coming within the scope of this invention. In the table, column 1 gives the name of the drugs, column 2, the vehicle, column 3, the concentration; column 4, the number of animals used; and columns 5, the final score.

TABLE 1

Topical Treatment

| Name of Compound | Vehicle* | % Conc. | No. Animals | Final Score |
|---|---|---|---|---|
| 5-Methylthio-7-chloro-2,3-dihydroimidazo[1,2-c]pyrimidine hydrochloride | R | 2.5 | 4 | 2.00 |
| 5-Methylthio-7-chloro-8-phenyl-2,3-dihydroimidazo[1,2-c]pyrimidine hydrochloride | D | 2.5 | 4 | 1.97 |
| 5-Methyl-7-chloro-2,3-dihydroimidazo[1,2-c]pyrimidine hydrochloride | K | 1.0 | 4 | 1.95 |
|  | D | 1.0 | 4 | 1.56 |
|  | B | 1.0 | 4 | 2.06 |
|  | R | 1.0 | 4 | 1.81 |
| 3-Phenyl-5-methyl-7-chloro-2,3-dihydroimidazo[1,2-c]pyrimidine hydrochloride | D | 2.5 | 4 | 1.72 |
| 5-Ethyl-7-chloro-2,3-dihydroimidazo[1,2-c]pyrimidine hydrochloride | D | 2.5 | 3 | 1.60 |
|  | D | 1.0 | 4 | 1.09 |
|  | D | 1.5 | 4 | 1.53 |

A second in-vivo test against Herpes simplex virus type I and Herpes simplex virus type II was carried out as follows. Guinea pigs were inoculated intravaginally by swabing the vagina with an absorbent cotton swab containing $2 \times 10^4$ plaque forming units of the virus. Prior to the inoculation with the virus, the vagina was swabbed with physiological saline to remove potential virus inhibitors. Treatment was started four hours after inoculation and continued for four days. The drug in a suitable base was introduced into the vaginal area also with an absorbent cotton swab. Controls in which the vehicle only were swabbed were included. Beginning on day 5 after inoculation and continuing through day 10, each animal was examined and scored from 0 to 4+ for secretion, inflammation, vesiculation and necrosis, thus yielding a possible top score of +16 per guinea pig. The results of this determination are included in Table 2. In the table, column 1 gives the name of the compound; column 2, the vehicle; column 3, the concentration; column 4, the number of animals used; and columns 5, the final score.

TABLE 2

Intravaginal Treatment

| Name of Compound | Vehicle* | % Conc. | No. Animals | Final Score |
|---|---|---|---|---|
| N-(β-Chloroethyl)-7-amino-8-nitro-2,3-dihydroimidazo[1,2-c]pyrimidine hydrochloride | R | 2.5 | 4 | 1.25 |
| 5-Methylthio-7-chloro-2,3-dihydroimidazo[1,2-c]pyrimidine hydrochloride | R | 2.5 | 4 | .92 |
|  | D | 2.5 | 4 | 3.81 |
| 5-Methyl-7-chloro-2,3-dihydroimidazo[1,2-c]pyrimidine hydrochloride | C | 2.5 | 5 | 7.9 |
|  | D | 2.0 | 5 | 6.13 |
|  | R | 2.0 | 4 | 3.17 |
|  | R | 2.0 | 5 | 3.57 |
| 5-Ethyl-7-chloro-2,3-dihydroimidazo[1,2-c]pyrimidine hydrochloride | R | 2.5 | 4 | 2.83 |

*See Table 4

The compounds of this invention also have anti-viral activity in vitro against Herpes simplex virus. In order to demonstrate this activity, the following test method was employed.

African green monkey kidney cells (BSC-1) or Hela cells (5-3) were grown in 25 cc. Falcon flasks at 37° C. in medium 199 with 5 percent inactivated fetal bovine serum (FBS), penicillin (150 units 1 ml.) and streptomycin (150 mcg./ml.). When confluent monolayers were formed, the supernatant growth medium was removed and 0.3 ml. of an appropriate dilution of Herpes simplex virus was added to each flask. After adsorption for one hour at room temperature, the virus infected cell sheet was overlaid with a medium comprising one part of 1 percent Ionagar No. 2 and one part double strength medium 199 with FCS, (fetal calf serum) penicillin, and streptomycin and also containing drug at concentrations of 100, 50, 25, 12, 6 and 3 micrograms per milliliter (mcg./ml.). The flask containing no drug served as a control. The stock solutions of 2,3-dihydroimidazo[1,2-c]pyrimidine compounds were made up in dimethylsulfoxide dilution at a concentration of $10^4$ mcg./ml. The flasks were incubated for 72 hours at 37° C. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque inhibition. Table 3, which follows, embodies the results of these determinations. In the table, column 1 gives the name of the compound, columns 2 through 6, the percent inhibition of herpes simplex plaques at various mcg./ml. levels of drug.

TABLE 3

| Name of Compound | PERCENT INHIBITION OF PLAQUES AT | | | | | |
|---|---|---|---|---|---|---|
|  | 100 mcg/ml | 50 mcg/ml | 25 mcg/ml | 12 mcg/ml | 6 mcg/ml | 3 mcg/ml |
| 5-Methyl-7-chloro-2,3-dihydroimidazo[1,2-c]pyrimidine hydrochloride | T | 85 | 0 | 0 | 0 |  |
|  | T | 82 | 11 |  |  |  |
| 5-n-Amyl-7-chloro-2,3-dihydroimidazo[1,2-c]pyrimidine hydrochloride | T | 100 ST | 29 | 0 | 0 | 0 |
|  | T | 100 ST | 87 | 41 | 0 |  |
| 5-Ethyl-7-chloro-2,3-dihydroimidazo[1,2-c]pyrimidine hydrochloride | T | 100 | 50 | 10 | 0 | 0 |
|  | 100 ST | 76 | 33 | 30 | 33 | 0 |
| 5-Amino-7-chloro-2,3-dihydroimidazo[1,2-c]pyrimidine hydrochloride |  | 11 | 0 | 0 | 0 | 0 |

TABLE 3-continued

| Name of Compound | PERCENT INHIBITION OF PLAQUES AT | | | | | |
|---|---|---|---|---|---|---|
| | 100 mcg/ml | 50 mcg/ml | 25 mcg/ml | 12 mcg/ml | 6 mcg/ml | 3 mcg/ml |
| N,5-Dimethyl-7-amino-2,3-dihydroimidazo[1,2-c]pyrimidine dihydrochloride | 30 | 18 | 27 | 0 | 0 | |
| N,5-Dimethyl-7-benzylamino-2,3-dihydroimidazo[1,2-c]pyrimidine hydrochloride | 9 | 0 | 0 | 0 | 0 | |
| 5-Methylthio-7-chloro-2,3-dihydroimidazo[1,2-c]pyrimidine hydrochloride | T / T | T / T | T / T | 100 / T | 49 / 48 | 30 |
| 5-Methylthio-7-chloro-8-phenyl-2,3-dihydroimidazo[1,2-c]pyrimidine hydrochloride | T / T | T / T | T / T | T / T | T / T | 100 ST / 58 |
| 5-Methyl-7-pyrrolidino-2,3-dihydroimidazo[1,2-c]pyrimidine hydrochloride | 7 | 0 | 0 | 0 | 0 | 0 |
| (±) 3-Phenyl-5-methyl-7-chloro-2,3-dihydroimidazo[1,2-c]pyrimidine hydrochloride | T / T | 100 ST / 95 | 78 / 68 | 4 / 23 | 0 / 0 | 0 / 0 |
| (±) 2-Phenyl-5-methyl-7-chloro-2,3-dihydroimidazo[1,2-c]pyrimidine hydrochloride | T / T | 100 ST / 89 | 87 / 83 | 41 / 50 | 0 / 13 | 0 / 0 |
| (±) 3,5-Dimethyl-7-chloro-2,3-dihydroimidazo[1,2-c]pyrimidine hydrochloride | T | 74 | 12 | 0 | 0 | |
| (±) 3-Phenyl-5-methylthio-7-chloro-2,3-dihydroimidazo[1,2-c]- | T LV / T HV | T / T | T / T | T / T | 100 / 84 | 57 / 23 |
| N-(β-Chloroethyl)-7-amino-8-nitro-2,3-dihydroimidazo[1,2-c]pyrimidine hydrochloride | MT | MT | 68 MT | 41 | 33 | |

MT - moderately toxic
T - toxic
ST - slightly toxic
LV - low virus input
HV - high virus input In accordance with the data presented in the above table, those compounds according to Formula I in which $R^1$ is chloro, form a preferred class of the compounds of this invention and more particularly, those compounds according to Formula I in which $R^1$ is chloro, and R is $C_1$–$C_5$ alkyl or methylmercapto constitute a particularly preferred group of compounds.

Compounds coming within the scope of Formula I above are above to suppress the growth of Herpes simplex virus on various surfaces wherein said virus is multiplying. These surfaces include non-living surfaces such as hospital glassware, hospital working surfaces and the like. The compounds can also be administered to mammals topically both to skin surfaces and particularly to mucuosal membranes such as those present in the oral cavities and in the vagina. For such topical application, any of the vehicles listed in Table 4 below may be employed. A particularly useful vehicle for application to mucuosal membranes is vehicle R, a cream base.

Table 4

| Vehicles From Tables 1 & 2 | |
|---|---|
| A = 75 percent DMSO | |
| B = Water | |
| C = Visible Difference composed of: (Unit Formula) | |
|    Isopropyl Myristate | 3% |
|    Polyethylene ether of stearyl alcohol (Polawax) | 8% |
|    Squalene | 3% |
|    Beeswax (White) | 1.5% |
|    Glycerine | 5% |
|    Preservatives | |
|    Purified Water q.s. to | 100% |
| D = Merthiolate Cream composed of: (Unit Formula) | |
|    1 part Thimerosal (optional) | |
|    150 parts Stearic Acid | |
|    25 parts Cetyl Alcohol | |
|    40 parts Mineral Oil | |

Table 4-continued

| Vehicles From Tables 1 & 2 |
|---|
|    100 parts Glycerin |
|    125 parts Triethanolamine |
|    10 parts Polyoxyethylene Sorbitan Monostearate |
|    Purified Water q.s. to 1000 parts |
| F = Zinc Oxide ointment |
| G = Amertan Jelly composed of: (Unit Formula) |
|    50 parts Tannic Acid (optional) |
|    100 parts Propylene Glycol |
|    22.55 parts Tragacanth |
|    0.2 parts Thimerosal |
|    Purified Water q.s. to 1000 parts |
| I = Suppositories |
| P = Mem with Hanks salts, 1 percent FCS, pen-strep and Glutamine |
| O = media 199 with FCS |
| R = Cream base without Merthiolate |

The particular pharmaceutical vehicle or carrier for the antiviral agents of formula I should be nonirritating either to skin or mucosa. Obviously, in general, skin can tolerate a greater degree of irritation in a carrier than can mucosa, but care should be taken in selection of a carrier that it be non-irritating for the particular body surface, internal or external, to which it is to be applied.

For treatment of Herpes simplex infections of the skin or mucosal surfaces, a compound of this invention is applied to the infected area as a 0.5–2.5% solution or suspension of an antiviral drug in salt form according to formula I above. The concentration of drug should be such that an anti-Herpes quantity can readily be delivered by application to the infected site of a thin layer of drug-containing vehicle. Whether it be a cream base, a jelly, or a high-viscosity aqueous vehicle.

I claim:

1. A compound of the formula:

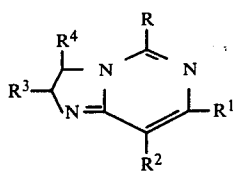

wherein R is H, $C_1$–$C_5$ alkyl, amino, phenyl or $CH_3$—S, $R^1$ is Cl, and $R^2$, $R^3$ and $R^4$ individually are H, methyl or phenyl with the proviso that R is H only when one of $R^3$ and $R^4$ is methyl, and pharmaceutically-acceptable acid addition salts thereof formed with strong acids.

2. A compound according to claim 1, said compound being 5-methyl-7-chloro-2,3-dihydroimidazo[1,2-c]pyrimidine.

3. The hydrochloride salt of the base of claim 2.

4. A compound according to claim 1, said compound being 5-methylthio-7-chloro-2,3-dihydroimidazo[1,2-c]pyrimidine.

5. The hydrochloride salt of the base of claim 4.

6. A compound according to claim 1, said compound being 5-thiomethyl-7-chloro-8-phenyl-2,3-dihydroimidazo[1,2-c]pyrimidine.

7. The hydrochloride salt of the base of claim 6.

8. A compound according to claim 1, said compound being 3-phenyl-5-methyl-7-chloro-2,3-dihydroimidazo[1,2-c]pyrimidine.

9. The hydrochloride salt of the base of claim 8.

10. A compound according to claim 1, said compound being 5-ethyl-7-chloro-2,3-dihydroimidazo[1,2-c]pyrimidine.

11. The hydrochloride salt of the base of claim 10.

12. The process of treating Herpes simplex infections on skin or mucosal membranes which comprises applying to said infected surface an anti-Herpes concentration of a compound according to claim 1 in a non-irritating vehicle.

13. A pharmaceutical composition in unit dosage form for the topical treatment of Herpes simplex infections consisting of a non-irritating pharmaceutical carrier and as its therapeutic agent, 0.5–2.52 of a compound according to claim 1.

14. N-($\beta$-Chloroethyl)-7-amino-8-nitro-2,3-dihydroimidazo[1,2-c]pyrimidine and its pharmaceutically acceptable acid addition salts.